US005693350A

United States Patent [19]
Fernandez et al.

[11] Patent Number: 5,693,350
[45] Date of Patent: Dec. 2, 1997

[54] PROCESS FOR PREPARING A MEAT PATE HAVING A LOW FAT CONTENT

[75] Inventors: Isabel Fernandez, Montbazon; Marcel Alexandre Juillerat, Fondettes, both of France; Rao Mandava, Helsingborg, Sweden

[73] Assignee: Nestec S.A., Vevey, Switzerland

[21] Appl. No.: 664,274

[22] Filed: Jun. 11, 1996

[30] Foreign Application Priority Data

Jun. 16, 1995 [EP] European Pat. Off. ............ 95201617

[51] Int. Cl.$^6$ .................................................. A23L 1/317
[52] U.S. Cl. ........................ 426/58; 426/59; 426/646; 426/802
[58] Field of Search .......................... 426/56, 58, 59, 426/104, 574, 646, 802, 804

[56] References Cited

U.S. PATENT DOCUMENTS 5,232,722  8/1993  Obara et al. .................... 426/104

FOREIGN PATENT DOCUMENTS

| 840944 | 5/1970 | Canada | 426/58 |
| 0278427 | 2/1988 | European Pat. Off. | |
| 0632963 | 5/1994 | European Pat. Off. | |
| 2681511 | 3/1993 | France | 426/646 |
| 6-121656 | 5/1994 | Japan | 426/646 |
| 1692524 | 11/1991 | U.S.S.R. | 426/646 |
| 1729403 | 4/1992 | U.S.S.R. | 426/646 |
| 94/22331 | 10/1994 | WIPO | |

OTHER PUBLICATIONS

Giese, "Developing Low–Fat Meat Products", *Food Technology*, Apr., 1992, pp. 100–108, 426/646.
MacFarlane et al, "Binding of Comminuted Meat: Effect of High Pressure", *Meat Science* 10 (1984), pp. 307–320, 426/646.
MacFarlane, "Pressure Induced Solubilization of Meat Proteins In Saline Solution", *J. Food Science*, vol. 39 (1974), pp. 542–547, 426/646.
"Effects of High Hydrostatic Pressure on Characteristics of Pork Slurries and Fractivation of Microorganisms Associated with Meat and Meat Products".
Shigehisa et al, *Int'l J. of Food Microbiology*, 12 (1991), pp. 207–215, 426/646.
Patent Abstracts of Japan, vol. 18, No. 71, Feb. 7, 1994.
Database WPI, Week 9528, JP-A-07 123,949, 16 May, 1995.
Database WPI, Week 7742, JP-A-50 121,485, 23 Sep., 1975.

*Primary Examiner*—Arthur L. Corbin
*Attorney, Agent, or Firm*—Pennie & Edmonds

[57] ABSTRACT

Process for the preparation of a meat pâté having a low fat content, in which a meat emulsion is prepared by combining at least meat, water, salts and a fat substitute, the emulsion is subjected to proteolytic digestion, cooked at a temperature of between 65° and 75° C. and the subjected to a hydrostatic pressure greater than 400,000 kPa at a temperature of between −10° and 75° C. for a time sufficient to obtain less than 4.5 protease units per g of pâté, thus forming a low fat content pâté.

8 Claims, No Drawings

PROCESS FOR PREPARING A MEAT PATE HAVING A LOW FAT CONTENT

TECHNICAL FIELD

The present invention relates to a process for the preparation of a pâté having a low fat content combining at least meat, water, salts and a fat substitute.

BACKGROUND

European patent application ("EP") 683986 describes a process in which a hydrostatic pressure of between 500 and 400,000 kPa is applied to a meat mixture for sausages, before cooking, so as to enhance the cooking yield of the sausage and the firmness of its texture.

Likewise, EP 278427 describes a process for the preparation of a sterilized meat pâté in which a meat emulsion is prepared, subjected to proteolytic digestion with technical proteases, packaged hermetically, then subjected to cooking at boiling temperature. The pâté obtained by this process thus exhibits a much better spreadability than that of sterilized traditional pâtés not having undergone proteolytic digestion.

However, the cooking of the emulsion at boiling temperature, that is to say at temperatures close to 100° C., causes evaporation of water therefrom which induces contraction of the final texture of the pâté and therefore a decrease in its spreadability. Furthermore, it also appears clearly that the cooking of the digested emulsion at boiling temperature is the only sufficient means of inactivating the activity of proteases. Thus, there remains a need for low fat content meat pâtés that have good spreadability.

SUMMARY OF THE INVENTION

The present invention is directed to a process for the preparation of a meat pâté having a low fat content which exhibits a texture and a spreadability superior to that of traditional pâtés having a low fat content. The texture and spreadability are preserved during storage of the pâté.

To this end, in the process according to the invention, a meat emulsion is prepared by combining at least meat, water, salts and a fat substitute, the emulsion is subjected to proteolytic digestion, cooked at a temperature of between 65° and 75° C. and then subjected to a hydrostatic pressure greater than 400,000 kPa at a temperature of between −10° and 75° C. for a time sufficient to obtain less than 4.5 protease units per g of pâté.

Surprisingly, the proteases of a meat emulsion or of a pâté, endogenous or exogenous, can be inactivated by the sole treatment at a high hydrostatic pressure without the need for protease inhibitors or for a high temperature, for example. A treatment at a hydrostatic pressure greater than 400,000 kPa may thus inactivate more than 97% of the initial proteolytic activity of the emulsion.

Surprisingly, a residual proteolytic activity in a pâté according to the invention of less than 4.5 units/g is also not sufficient to cause undesirable softening of the pâté during its storage. Thus, a pâté according to the invention may be stored for at least 60 days without observing a decrease in its spreadability or a significant increase in its bitterness.

Furthermore, the pâté according to the invention spreads particularly well in the plate, and even spreads better than traditional pâtés having a low fat content, in which the fat has been replaced with a fat substitute. Indeed, fat substitutes, such as starch, hydrocolloids and animal or plant proteins, for example, unfortunately do not confer on a pâté having a low fat content a spreadability as good as that conferred by fat.

Likewise, the present process also has the advantage of not causing excessive evaporation of water from the pâté during cooking, which would induce contraction of the texture of the pâté and therefore a decrease in its spreadability. Indeed, cooking of an emulsion according to the invention at low pressure and at a temperature greater than 75° C., especially at 80° C., or more causes undesirable contraction of the texture of the pâté (see "Comparative examples").

Likewise, cooking an emulsion according to the invention at high pressure (greater than 100,000 kPa) and at 65°–75° C. also causes undesirable contraction of the texture of the said pâté (see section "Comparative examples"). These results support the novelty of the present process because by separating the cooking and the inactivation of the proteases, a pâté can be obtained which has a good spreadability. Furthermore, unexpectedly, it is also possible to cook an emulsion according to the invention at 65°–75° C. (at low pressure) then to inactivate the proteases in the pâté at high pressure and at a cooking temperature (up to 75° C.) without the pâté exhibiting undesirable contraction of its texture.

DETAILED DESCRIPTION OF THE INVENTION

In the description, the expression "pâté having a low fat content" designates pâtés having a total fat content of less than 10%. Thus, the present pâté preferably comprises 40 to 80% ground lean meats generally comprising 3°–8% fat, 1 to 15% of a fat substitute, 15–50% added water, 1.2–2.4% nitrite salts and up to 0.3% phosphates.

Likewise, the percentages are given by weight unless otherwise stated, which means that the quantity of the various ingredients are given by weight relative to the final weight of emulsion. Furthermore, the pressure is given in absolute pressure, a low pressure being a pressure of less than 100,000 kPa, preferably 100 to 500 kPa, and a high pressure being a pressure greater than 100,000 kPa, preferably greater than 400,000 kPa. Finally, the enzyme activity units of the proteases are given in μg of substrates converted per min.

To carry out the present process, a meat emulsion having a low fat content comprising at least meat, water, salts and at least one fat substitute is therefore prepared. Preferably, this emulsion comprises 40 to 80% finely ground lean meats, 15–50% water, 1.2 to 2.4% nitrite salts, up to 0.3% phosphates, 1 to 15% of at least one fat substitute and spices such as, for example, pepper, ginger, coriander and ascorbic acid. Finally, the preparation of this emulsion may be completely traditional, in the sense that all of these constituents can be mixed in a conventional mincer until an emulsion is obtained, for example.

In a second stage, the said emulsion is subjected to proteolytic digestion. The enzymes responsible for this digestion may be endogenous proteases of the meat tissues which are activated by subjecting the emulsion to a temperature favorable to the activity of these proteases for a time sufficient to observe a quantifiable release of peptides and amino acids (quantifiable on a conventional chromatography gel, for example). Incorporating into the meat emulsion offal parts which naturally comprise proteases may also be envisaged.

However, it is preferable to add technical proteases to the meat emulsion, that is to say a preparation comprising at least one type of protease, such as papain, trypsin, pancreatin of animal pancreas, and also various microbial proteases obtained, for example, from Bacillus subtilis, and fungal proteases obtained, for example, from *Aspergillus oryzae*, which are commercially available. The technical proteases may be added during the preparation of the emulsion, in the form of a mixture of a powder or of a concentrated solution of protease with all or part of the water which is used in the preparation of emulsion, for example. It may also be envisaged mixing the proteases with ice, in place of all or part of the water, so as to cool the emulsion and to be able to thus control the activity of the proteases, for example. In this manner, the meat emulsion is subjected to a controlled digestion with these enzymes, preferably for 10 to 120 min at a temperature favorable to the activity of the proteases, that is to say generally at a temperature of between 30° and 60° C.

In a third stage, the meat emulsion thus digested is cooked at a temperature of between 65° and 75° C. The optimum cooking temperature will then depend on the composition of the emulsion and on the dry or moist atmosphere cooking system, for example. However, in general, it is preferable to choose a cooking temperature such that the final pâté does not lose more than 5% water by evaporation. The cooking temperatures most commonly used may thus be between 68°–72° C. and may be applied for 1 to 60 min, for example.

It should be noted that the cooking is not sufficient to inactivate the activity of the proteases. Indeed, even a temperature of 80° C. is not sufficient to inactivate particularly resistant proteases. Furthermore, if the cooking temperature is raised above 75° C. in order to inactivate them sufficiently, excessive evaporation of water in the pâté and an undesirable modification of its texture are most often caused.

In the present process, the cooked emulsion is then subjected to a hydrostatic pressure greater than 400,000 kPa at a temperature of between −10° and 75° C., for a time sufficient to obtain less than 4.5 protease units per g of pâté, preferably less than 3.8 units/g.

It should be noted that the proteases, depending on their origins, may have completely different resistance to inactivation by the high pressure, and that the intensity of the applied pressure is inversely proportional to the duration of treatment. However, in general, most of the proteases in a pâté or in an emulsion can be sufficiently inactivated at a hydrostatic pressure greater than 400,000 kPa, but preferably greater than 500,000 kPa, applied for 1 to 60 min, for example.

Finally, in order to apply the high pressure, it is not necessary to use special gases or inhibitors. A hydrostatic pressure, that is to say a pressure transmitted by a liquid, is applied to the food material. For that, this material can be isolated from the liquid used to transmit the high pressure, for example water or oil, by means for packaging the food under vacuum, especially in deformable plastic or aluminium containers, for example. These containers may then be placed in a chamber of a high pressure device in which the high-pressure treatment is applied for a time and at a temperature sufficient to obtain inactivation of the enzymes.

The treatment time may be greater than 30 min, and preferably greater than 10 min. Furthermore, this treatment time starts from the moment when the desired temperature and pressure are reached, the time necessary to reach these values being on average of the order of 1 min, for example.

In a specific embodiment of the present process, the said emulsion is prepared by finely grinding the meat in the presence of salts, while adding water, a preparation comprising at least one technical protease and the said fat substitute, the meat emulsion thus obtained is packaged under vacuum, the packaged emulsion is subjected to the digestion at a temperature favorable to the activity of proteases, the hydrolysed emulsion is cooked at a temperature of between 65° and 75° C. as described above, and then is subjected to the said high hydrostatic pressure, at a temperature of between −10° and 75° C., before unpacking.

EXAMPLES

The process according to the present invention is described in greater detail in the examples presented below by way of illustration. These examples are preceded by a description of two tests which make it possible to measure the activity of a protease, and the spreadability and the bitterness of a pâté , as well as four comparative examples.

Activity of a Protease

The activity of a protease, and especially that of trypsin, is determined with the aid of a "protease gels tablet" kit (Biorad).

For that, a sample of emulsion or of meat pâté is placed in a well of a 1% agarose gel comprising bovine casein prepared in a Tris buffer at pH 7.2, the gel is incubated overnight at 25° C., the diameter of diffusion of the protease, characterized by a transparent halo around the well resulting from the digestion of the casein, is measured and then the activity of the protease is determined in relation to a standard curve established by the same test and at the same time with samples of the same protease having known enzyme activity units.

The results presented in the examples below are given in residual protease units per g of pâté relating to the initial units per g of emulsion. Bitterness and spreadability of a pâté

Assessment of the bitterness and the spreadability of a pâté were performed by a panel of about 30 people. The tests were carried out according to a double blind design so as to obtain reproducible results. Each person thus marked, according to a scale, the characteristics of a pâté between 1 and 5. The marks presented in the examples below result from the mean of the marks given by each person on the panel.

For the bitterness, the value 1 means that the pâté is less bitter or milder than the other pâtés, while the value 5 means the contrary. The marks given to the pátés in accordance with the present invention are between 1 and 2.5.

For the spreadability, the value 1 means that the pâté is firmer and less spreadable than the other pâtés, while the value 5 means that the pâté is softer and more spreadable than the others. The marks given to the pátés in accordance with the present invention are between 2.3 and 3.1.

Comparative Examples

Pâtés having a low fat content are prepared from an aqueous meat emulsion comprising 60% lean meats (5% animal fats), 18% pig liver, 17.5% ice, 1.5% nitrite salts, 0.3% phosphates, 2% starch, 0.7% spices and 30 mg/kg of trypsin (5100 units/mg of trypsin).

For that, the meat is finely minced in the presence of the salts and the phosphate in a conventional mincer for 1 min, the ice and a preparation comprising trypsin dissolved in water are added, the mixture is mixed until the temperature of the emulsion reaches 4° C., the starch and the spices are added and the mixture is mixed until the temperature of the emulsion reaches 14° C.

50 to 100 g of emulsion are then distributed into individual plastic bags, the bags are sealed under vacuum, these bags are subjected to a temperature of 42° C., which is favourable to the activity of trypsin, for 1 h and then the activity of the trypsin is measured in one of the bags by the test described above.

A portion of the bags is subjected to cooking at 70° C. for 30 min, another portion to cooking at 70° C. for 60 min, another portion to cooking at 80° C. for 60 min and another portion to 700,000 kPa at 70° C. for 30 min.

Finally, the pátés are stored at a refrigeration temperature (5°–12° C.) for 60 days, then the residual activity of the trypsin, the bitterness and the spreadability of the pátés are determined by the tests described above. The results are presented in Table 1 below.

TABLE 1

| Comparative example: cooking | Residual units/g of pâté (60 days) | Bitterness (60 days) | Spreadability (60 days) |
| --- | --- | --- | --- |
| 1: 70° C./30 min | 25.4 | 3.5 (bitter) | 3.6 (soft) |
| 2: 70° C./60 min | 9.9 | 2.9 | 3.2 |
| 3: 80° C./60 min | 2.2 | 1.5 | 2.2 |
| 4: 70° C./30 min/ 700,000 kPa | 1.7 | 2.1 (mild) | 1.0 (firm) |

(Pátés assessed: bitterness 1–2.5; spreadability 2.3–3.1)

As can be seen, the pátés cooked at atmospheric pressure at 70° C. have a residual trypsin activity greater than 3% of that initially present in the emulsion. This activity caused extensive hydrolysis, of the proteins, which led, after 60 days of storage, to excessive softening of the pátés and to their being made bitter (the small peptides confer the bitterness).

In addition, the pátés cooked at atmospheric pressure at 80° C. or at 700,000 kPa at 70° C. have a residual trypsin activity less than 3% of that initially present in the emulsion. This activity is not sufficient to make the pâté bitter and to cause excessive softening therein after 60 days of storage. However, both types of cooking caused contraction of the final texture of the pâté, probably due to excessive denaturation of the proteins, which led the pátés to be too firm compared with the pátés according to the present invention.

Examples 1 and 2

Two meat pátés are prepared from a meat emulsion comprising 60% lean meats (5% animal fats), 18% pig liver, 17.5% ice, 1.5% nitrite salts, 0.3% phosphates, 2% starch, 0.7% spices and 30 mg/kg of trypsin (5100 units/mg of trypsin).

For that, the meat is finely minced in the presence of the salts and the phosphate in a conventional mincer for 1 min, all the ice and a preparation comprising trypsin dissolved in the remainder of the water are added, the mixture is mixed until the temperature of the emulsion reaches 4° C., the starch and the spices are added and the mixture is mixed until the temperature of the emulsion .reaches 14° C.

50 to 100 g of emulsion are then distributed into individual plastic bags, the bags are sealed under vacuum, these bags are subjected to a temperature of 42° C., which is favourable to the activity of trypsin, for 1 h and then the activity of the trypsin in the emulsion is measured by the test described above.

In the first example, a portion of the bags is cooked at a temperature of 70° C. for 30 min, they are subjected to a hydrostatic pressure of 500,000 kPa for 10 min at a temperature of 75° C., the pâté is stored for 60 days at a refrigeration temperature, then the residual activity of the trypsin, the bitterness and the spreadability of the pátés are determined by the tests described above. The results are presented in Table 2 below.

In the second example, a portion of the bags is cooked at a temperature of 70° C. for 30 min, they are subjected to a hydrostatic pressure of 700,000 kPa for 10 min at a temperature of 60° C., the pâté is stored for 60 days at a refrigeration temperature, then the residual activity of the trypsin, the bitterness and the spreadability of the pátés are determined by the tests described above. The results are presented in Table 2 below.

TABLE 2

| Example | Activity units/g of pâté (60 days) | Bitterness (60 days) | Spreadability (60 days) |
| --- | --- | --- | --- |
| 1 | 3.8 | 2.1 | 2.3 |
| 2 | 1.8 | 2 | 2.5 |

(Pátés assessed: bitterness 1–2.5; spreadability 2.3–3.1)

These results confirm that a meat emulsion having a low fat content, hydrolysed enzymatically, cooked and inactivated at high pressure, gives a pâté having a smoothness in the mouth and a spreadability which are particularly appreciated by taste panels.

What is claimed is:

1. A process for the preparation of a meta pâté having a low fat content, which comprises the steps of preparing a meat emulsion by combining at least meat, water, salts and a fat substitute, subjecting the emulsion to proteolytic digestion, cooking the emulsion at a temperature of between 65° and 75° C., and then subjecting the emulsion to a hydrostatic pressure greater than 400,000 kPa at a temperature of between −10° and 75° C. for a time sufficient to obtain a residual proteolytic activity of less than 4.5 protease units per g of pâté, thus forming a low fat content pâté.

2. The process according to claim 1, in which the proteolytic digestion is conducted using endogenous proteases in the meat or with at least one technical protease.

3. The process according to claim 2, wherein the emulsion is prepared by finely grinding meat in the presence of salts, while adding water or ice, a preparation comprising at least one technical protease and the said fat substitute, the meat emulsion thus obtained is packaged under vacuum, and the packaged emulsion is then subjected to the proteolytic digestion cooking and pressure steps.

4. The process according to claim 3, wherein the hydrostatic pressure is applied for 1 to 60 minutes.

5. The process according to claim 3, wherein the cooking temperature is between 68° and 72° C.

6. The process according to claim 3, wherein the emulsion is subjected to digestion with a technical protease for 10 to 120 minutes at a temperature which is favorable to the activity of the protease.

7. The process according to claim 1, wherein the emulsion comprises 40 to 80% finely ground meat, 15 to 50% water or ice, 1.2 to 2.4% nitrite salts, up to 0.3% phosphates and 1 to 15% of the fat substitute.

8. The process according to claim 1, which further comprises selecting the fat substitute from the group consisting of starch, plant proteins, animal proteins or hydrocolloids.

* * * * *